US009239393B2

(12) United States Patent
Teshigawara et al.

(10) Patent No.: US 9,239,393 B2
(45) Date of Patent: Jan. 19, 2016

(54) POSITRON EMISSION COMPUTED TOMOGRAPHY APPARATUS AND IMAGE PROCESSING APPARATUS (71) Applicants: Manabu Teshigawara, Otawara (JP); Yasuhiro Noshi, Otawara (JP); Takuzo Takayama, Utsunomiya (JP)

(72) Inventors: Manabu Teshigawara, Otawara (JP); Yasuhiro Noshi, Otawara (JP); Takuzo Takayama, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 296 days.

(21) Appl. No.: 13/688,531

(22) Filed: Nov. 29, 2012

(65) Prior Publication Data

US 2013/0134314 A1 May 30, 2013

(30) Foreign Application Priority Data

Nov. 30, 2011 (JP) ................................ 2011-262756

(51) Int. Cl.
*G01T 1/29* (2006.01)
*G01T 1/164* (2006.01)
*A61B 6/03* (2006.01)

(52) U.S. Cl.
CPC ............... *G01T 1/2985* (2013.01); *A61B 6/037* (2013.01); *G01T 1/1647* (2013.01)

(58) Field of Classification Search
CPC ........ A61B 6/032; A61B 6/037; A61B 6/541; G01T 1/2985; G01T 1/1647

USPC .......................................... 600/428; 382/107
See application file for complete search history.

(56) References Cited

U.S. PATENT DOCUMENTS

2007/0197927 A1\* 8/2007 Ofek ............................. 600/514
2012/0275657 A1\* 11/2012 Kolthammer et al. ........ 382/107

FOREIGN PATENT DOCUMENTS

JP 2005-195407 7/2005
JP 2007-3264 1/2007
JP 2009-156856 7/2009

\* cited by examiner

*Primary Examiner* — Yara B Green
(74) *Attorney, Agent, or Firm* — Oblon, McClelland, Maier & Neustadt, L.L.P.

(57) ABSTRACT

A positron emission computed tomography apparatus according to an embodiment includes a detector, a coincidence counting information generating unit, and a body movement detecting unit. The detector detects annihilation radiation released from a subject. The coincidence counting information generating unit searches for sets of counting information, which counted a pair of annihilation radiations at substantially the same time, from a counting information list that is generated from output signals of the detector; generates a set of coincidence counting information for each retrieved set of counting information; and generates a time series list of coincidence counting information. Based on the time series list of coincidence counting information, the body movement detecting unit detects temporal changes in the body movement of the subject.

9 Claims, 7 Drawing Sheets

| MODULE ID | SCINTILLATOR NUMBER (P) | ENERGY VALUE (E) | DETECTION TIME (T) |
|---|---|---|---|
| D1 | P11 | E11 | T11 |
| | P12 | E12 | T12 |
| | P13 | E13 | T13 |
| | ⋮ | ⋮ | ⋮ |

| MODULE ID | SCINTILLATOR NUMBER (P) | ENERGY VALUE (E) | DETECTION TIME (T) |
|---|---|---|---|
| D2 | P21 | E21 | T21 |
| | P22 | E22 | T22 |
| | P23 | E23 | T23 |
| | ⋮ | ⋮ | ⋮ |

| MODULE ID | SCINTILLATOR NUMBER (P) | ENERGY VALUE (E) | DETECTION TIME (T) |
|---|---|---|---|
| D3 | P31 | E31 | T31 |
| | P32 | E32 | T32 |
| | P33 | E33 | T33 |
| | ⋮ | ⋮ | ⋮ |

| COINCIDENCE NO. | SCINTILLATOR NUMBER (P) | ENERGY VALUE (E) | DETECTION TIME (T) | SCINTILLATOR NUMBER (P) | ENERGY VALUE (E) | DETECTION TIME (T) |
|---|---|---|---|---|---|---|
| 1 | P11 | E11 | T11 | P22 | E22 | T22 |
| 2 | P12 | E12 | T12 | P32 | E32 | T32 |
| 3 | P13 | E13 | T13 | P33 | E33 | T33 |
| ... | ... | ... | ... | ... | ... | ... |

POSITRON EMISSION COMPUTED TOMOGRAPHY APPARATUS AND IMAGE PROCESSING APPARATUS

CROSS-REFERENCE TO RELATED APPLICATIONS

This application is based upon and claims the benefit of priority from Japanese Patent Application No. 2011-262756, filed on Nov. 30, 2011; the entire contents of which are incorporated herein by reference.

FIELD

Embodiments described herein relate generally to a positron emission computed tomography apparatus and an image processing apparatus.

BACKGROUND

Typically, as a nuclear medicinal imaging apparatus, a positron emission computed tomography (PET) apparatus is known. During the imaging performed by a PET apparatus, a radiopharmaceutical agent that is labeled with positron-emitting radionuclides is administered to the subject. As a result, the positron-emitting radionuclides that are selectively incorporated into the body tissues of the subject release positrons, which then get coupled with electrons and are annihilated. At that time, the positrons release pairs of annihilation radiations (hereinafter, referred to as "annihilation gamma-rays) in the direction almost opposite. The PET apparatus detects such annihilation gamma-rays with the use of detectors that are arranged in a ring-like manner around the subject. Then, by referring to the detection result, the PET apparatus generates a time series list (also called "coincidence list") of coincidence counting information. Subsequently, with the use of the time series list of coincidence counting information, the PET apparatus performs reconstruction and generates a PET image.

Meanwhile, the methods of imaging performed by a PET apparatus include imaging in synchronization with the respiration of the subject. During the respiration-synchronized imaging, an external device other than the main body of the PET apparatus is used to obtain body movement information of the subject. The external device is, for example, a respiratory displacement monitor. Herein, for example, during the imaging, the respiratory displacement monitor emits infrared light to an infrared light reflection marker that is placed on the chest region of the subject; takes photographs using a reflection camera; and traces the marker shadow to obtain information on respiratory displacement. However, in the case of using such an external device, it becomes necessary to separately setup and adjust the external device. Moreover, since the infrared light reflection marker may move out of alignment or may fall down during the imaging, using it can be a complicated task.

DETAILED DESCRIPTION

Exemplary embodiments of a positron emission computed tomography apparatus and an image processing apparatus are described below in detail with reference to the accompanying drawings.

First Embodiment

In a first embodiment, a PET apparatus 100 does not make use of an external device such as a respiratory displacement monitor. Instead, the PET apparatus 100 obtains body movement information of the subject by means of direct processing for detection data. More particularly, from each set of coincidence counting information specified in a time series list of coincidence counting information, the PET apparatus 100 according to the first embodiment calculates each pair annihilation coordinate with the use of time of flight (TOF) information; and detects the temporal changes in the body movement of the subject based on the pair annihilation coordinates.

Herein, the body movement is detected by a body movement detecting unit 26 (described later). In the following description, firstly, a configuration of the PET apparatus 100 according to the first embodiment is explained; and that is followed by a detailed explanation of the operations performed by the body movement detecting unit 26.

Figure 1:
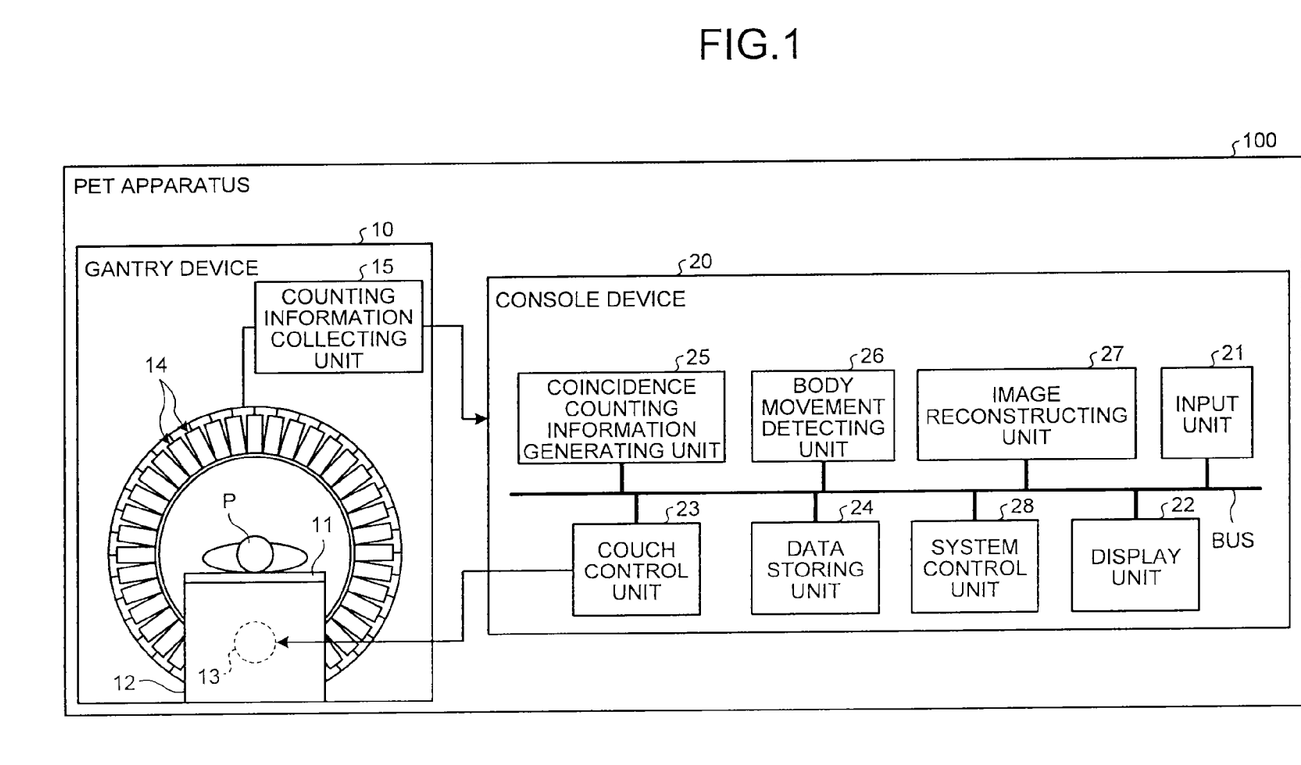
FIG. 1 is a block diagram illustrating a configuration of a PET apparatus according to a first embodiment.

FIG. 1 is a block diagram illustrating a configuration of the PET apparatus 100 according to the first embodiment. As illustrated in FIG. 1, the PET apparatus 100 according to the first embodiment includes a gantry device 10 and a console device 20.

The gantry device 10 detects pairs of annihilation gamma-rays, which are released from the positrons present inside a subject P, with the use of detectors that are arranged in a ring-like manner around the subject P. Then, the gantry device 10 generates counting information from the output signals of the detector and collects the counting information. As illustrated in FIG. 1, the gantry device 10 includes a couch top 11, a couch 12, a couch driving unit 13, a plurality of detector modules 14, and a counting information collecting unit 15. Moreover, as illustrated in FIG. 1, the gantry device 10 has a cavity that serves as a imaging region.

The couch top 11 is a bed on which the subject P is made to lie down. The couch top 11 is disposed on top of the couch 12. The couch driving unit 13 moves the couch top 11 under the control of a couch control unit 23 (described later). For example, the couch driving unit 13 moves the couch top 11 in such a way that the subject P moves in the imaging region of the gantry device 10.

The detector modules 14 detect the annihilation gamma-rays that are released from the positrons present inside the subject P. As illustrated in FIG. 1, the detector modules 14 are disposed to surround the subject P in a ring-like manner.

Figure 2:
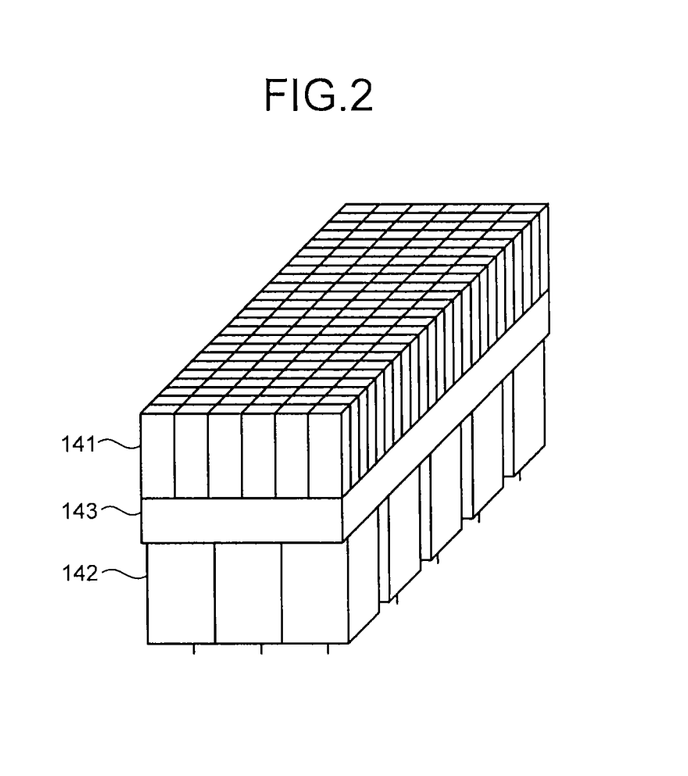
FIG. 2 is a diagram for explaining detector modules according to the first embodiment.

FIG. 2 is a diagram for explaining the detector modules 14 according to the first embodiment. As illustrated in FIG. 2, each detector module 14 is an Anger-type detector that implements the photon counting method, and includes scintillators 141, photomultiplier tubes (PMTs) 142, and a light guide 143.

The scintillators 141 convert the incident annihilation gamma-rays, which released from the positrons present inside the subject P, into scintillation photons (optical photons); and then output that. The scintillators 141 are formed with scintillator crystals suitable for TOF such as lanthanum bromide (LaBr3), lutetium yttrium oxyorthosilicate (LYSO), lutetium oxyorthosilicate (LSO), or lutetium gadolinium oxyorthosilicate (LGSO). As illustrated in FIG. 2, the scintillators 141 are arranged in a two-dimensional manner. The photomultiplier tubes 142 multiply the scintillation photons output from the scintillators 141 and convert it into electric signals. As illustrated in FIG. 2, a plurality of photomultiplier tubes 142 is arranged. The light guide 143 transmits the scintillation photons, which is output from the scintillators 141, to the photomultiplier tubes 142. The light guide 143 is, made of, for example, a plastic material having superior light permeability.

Each photomultiplier tube 142 includes a photocathode that receives scintillation photons and generates photoelectrons; a multi-stage dynode that applies an electric field so as to accelerate the photoelectrons; and an anode through which electrons outflow. The electrons that are released from the photocathode due to a photoelectric effect accelerate toward the dynode, collide with the surface of the dynode, and beat out a plurality of electrons. When this phenomenon is repeated across the multiple stages of the dynode; the number of electrons gets multiplied because of a chain-reaction-like manner, and the number of electrons in the anode reaches to about one million. Thus, in this example, the gain factor of each photomultiplier tube 142 becomes millionfold. Moreover, due to the multiplication in a chain-reaction-like manner, usually a voltage of 1000 volts or more gets applied between the dynode and the anode.

In this way, in the detector modules 14, the annihilation gamma-rays, which are released from the positrons present inside the subject P, are converted into scintillation photons by the scintillators 141; and the scintillator light is converted into electric signals by the photomultiplier tubes 142. With that, the detector modules 14 detect the annihilation gamma-rays released from the subject P.

Returning to the explanation with reference to FIG. 1, the counting information collecting unit 15 generates counting information from the output signals of the detector modules 14 and stores the counting information in a data storing unit 24 (described later). Meanwhile, although not illustrated in FIG. 1, the detector modules 14 are divided into a plurality of blocks, and the counting information collecting units 15 are disposed on a block-by-block basis. For example, in the first embodiment, since a single detector module 14 is considered to be a single block, the counting information collecting units 15 is disposed with respect to each detector module 14.

The counting information collecting unit 15 converts the output signals of the detector modules 14 into digital data and generates counting information. Herein, the counting information contains the detected positions, energy values, and detection time of the annihilation gamma-rays. For example, the counting information collecting unit 15 identifies a plurality of photomultiplier tubes 142 that have concurrently converted the scintillation photons into electric signals. Then, the counting information collecting unit 15 refers to the position of each identified photomultiplier tube 142 and the intensity of electric signals and accordingly calculates the position of the center of gravity; and then identifies scintillator numbers (P) that indicate the positions of the scintillators 141 on which the annihilation gamma-rays incident had occurred. Meanwhile, if the photomultiplier tubes 142 are capable of detecting positions, then the position identification can be performed by the photomultiplier tubes 142.

Moreover, the counting information collecting unit 15 performs integral calculation with respect to the intensity of electric signals that are output from each photomultiplier tube 142, and identifies energy values (E) of the incident annihilation gamma-rays on the detector modules 14. Furthermore, the counting information collecting unit 15 identifies detection times (T) taken for the detection of the annihilation gamma-rays by the detector modules 14. For example, the counting information collecting unit 15 identifies the detection times (T) with accuracy in the unit of $10^{-12}$ seconds (i.e., a picosecond). Herein, the detection times (T) can either be an absolute time or be the elapsed time since the start of imaging. In this way, the counting information collecting unit 15 generates counting information that contains the scintillator numbers (P), the energy values (E), and the detection times (T).

The console device 20 receives an operation performed by an operator with respect to the PET apparatus 100, and controls imaging of PET images as well as reconstructs the PET images with the use of the counting information collected by the gantry device 10. As illustrated in FIG. 1, the console device 20 includes an input unit 21, a display unit 22, the couch control unit 23, the data storing unit 24, a coincidence counting information generating unit 25, the body movement detecting unit 26, an image reconstructing unit 27, and a system control unit 28. Herein, the constituent elements of the console device 20 are interconnected via a bus.

The input unit 21 is a mouse or a keyboard that is used by the operator of the PET apparatus 100 to input various instructions and various settings. Then, the input unit 21 transfers the various instructions and the various settings to the system control unit 28. For example, the input unit 21 is used to receive an imaging start instruction. The display unit 22 is a monitor that is viewed by the operator, that displays a respiratory waveform of the subject and PET images, and that displays a graphical user interface (GUI) which enables the operator to input various instructions and various settings. The couch control unit 23 controls the couch driving unit 13.

Figure 3:
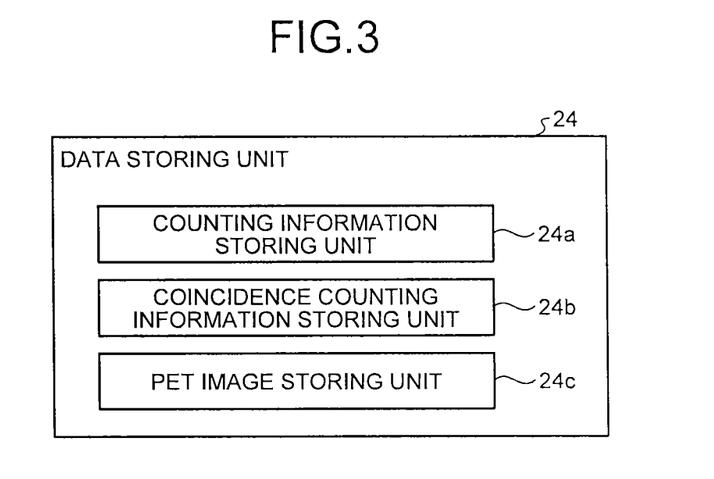
FIG. 3 is a diagram for explaining a data storing unit according to the first embodiment.

The data storing unit 24 is used to store a variety of data used in the PET apparatus 100. FIG. 3 is a diagram for explaining the data storing unit 24 according to the first embodiment. As illustrated in FIG. 3, the data storing unit 24 includes a counting information storing unit 24a, a coincidence counting information storing unit 24b, and a PET image storing unit 24c. Herein, the data storing unit 24 is configured with, for example, a semiconductor memory such as a random access memory (RAM) or a flash memory, or with a hard disk or an optical disk.

The counting information storing unit 24a is used to store the counting information that is collected by each counting information collecting unit 15. Herein, a list of sets of counting information that is stored in the counting information storing unit 24a is used during the operations performed by the coincidence counting information generating unit 25. Meanwhile, the list of sets of counting information that is stored in the counting information storing unit 24a can either be deleted after being used during the operations performed by the coincidence counting information generating unit 25 or be kept stored for a predetermined amount of time.

Figure 4:
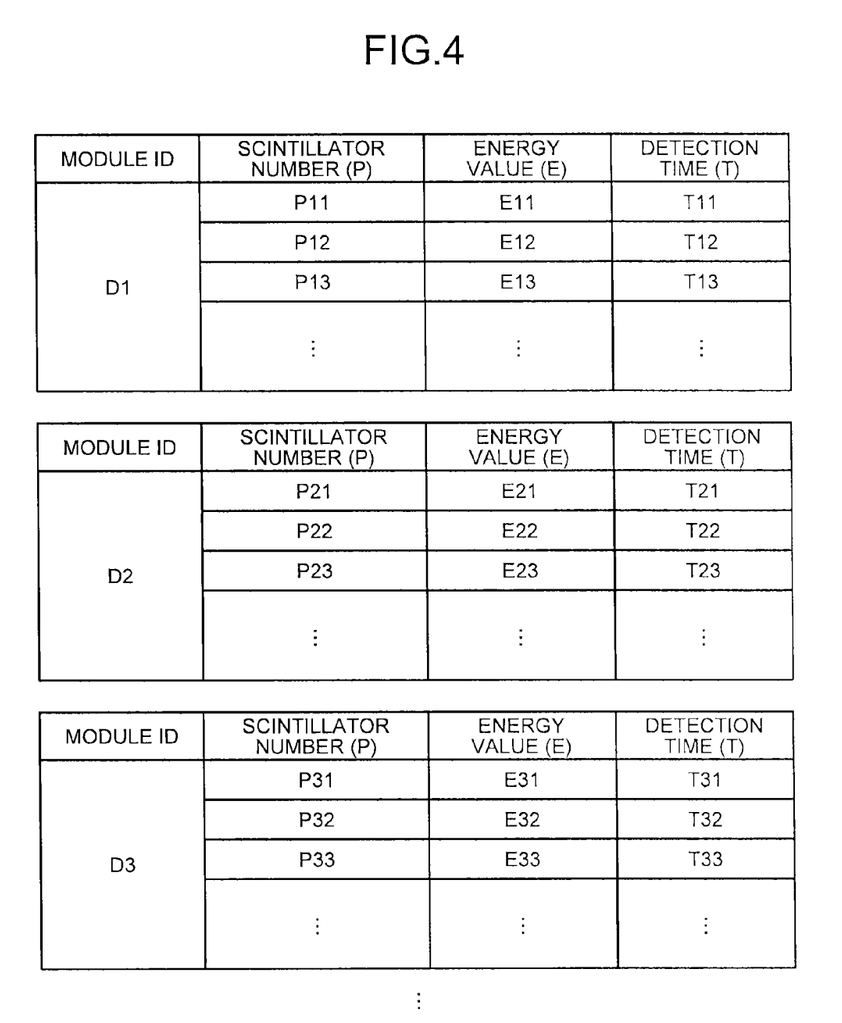
FIG. 4 is a diagram for explaining a list of sets of counting information according to the first embodiment.

FIG. 4 is a diagram for explaining the list of sets of counting information according to the first embodiment. As illustrated in FIG. 4, in the counting information storing unit 24a, the sets of counting information each containing the scintillator numbers (P), the energy values (E), and the detection times (T) are stored in a corresponding manner to module IDs that are used in identifying the detector modules 14.

The coincidence counting information storing unit 24b is used to store a time series list of coincidence counting information that is generated by the coincidence counting information generating unit 25. The time series list of coincidence counting information stored in the coincidence counting information storing unit 24b is used during the operations performed by the body movement detecting unit 26 and the image reconstructing unit 27. Meanwhile, the time series list of coincidence counting information stored in the coincidence counting information storing unit 24b can either be deleted after being used during the operations performed by the image reconstructing unit 27 or be kept stored for a predetermined amount of time.

Figure 5:
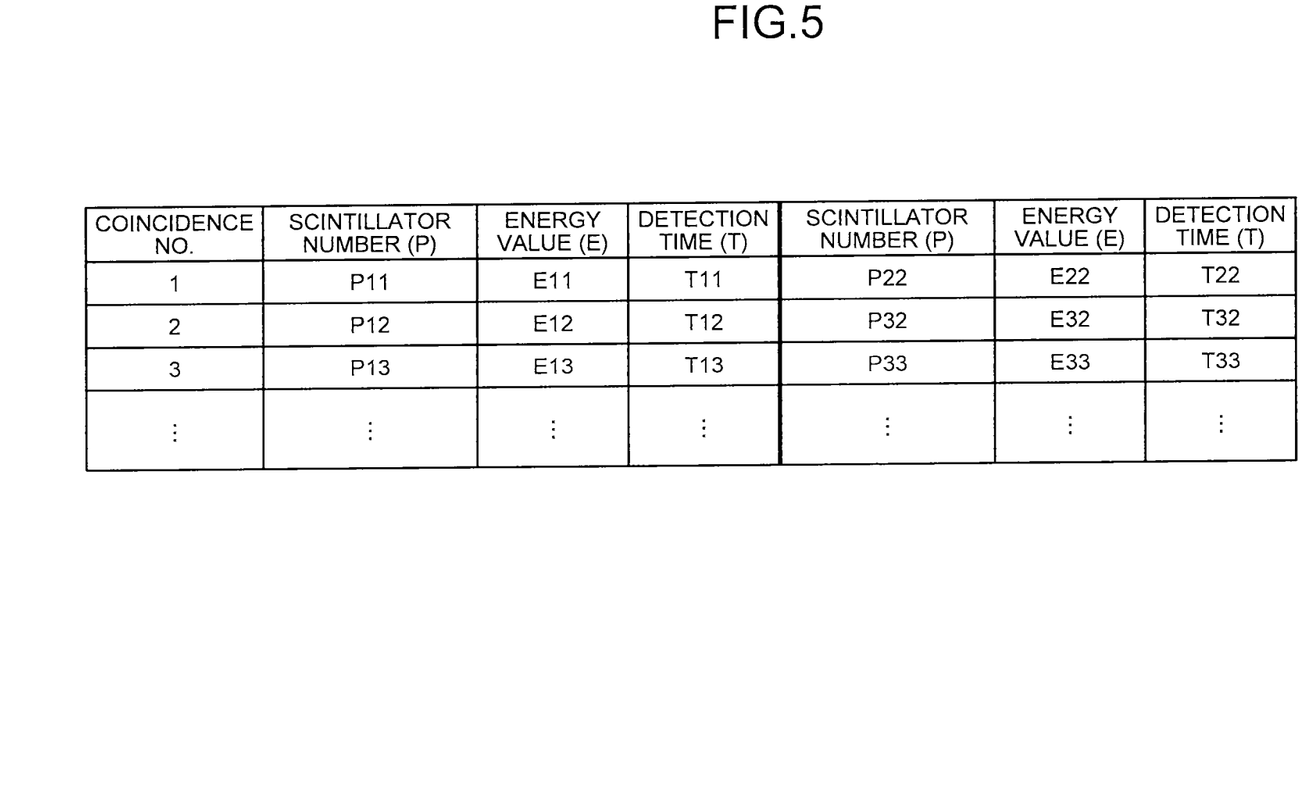
FIG. 5 is a diagram for explaining a time series list of coincidence counting information according to the first embodiment.

FIG. 5 is a diagram for explaining the time series list of coincidence counting information according to the first embodiment. As illustrated in FIG. 5, in the coincidence counting information storing unit 24b; sets of the counting information are stored in a corresponding manner to coincidence numbers that represent the serial numbers of the sets of coincidence counting information. In the first embodiment, the time series list of coincidence counting information is arranged roughly in the chronological order based on the detection times (T) of the sets of counting information.

The PET image storing unit 24c is used to store PET images that have been reconstructed by the image reconstructing unit 27. The PET images stored in the PET image storing unit 24c are displayed on the display unit 22 by the system control unit 28.

Returning to the explanation with reference to FIG. 1, the coincidence counting information generating unit 25 makes use of the list of sets of counting information counting information collected by the counting information collecting unit 15 and generates a time series list of coincidence counting information. More particularly, based on the detection times (T) of the sets of counting information, the coincidence counting information generating unit 25 searches for such sets of counting information, from the list of sets of counting information stored in the counting information storing unit 24a, which substantially concurrently counted the pairs of annihilation gamma-rays. Moreover, the coincidence counting information generating unit 25 generates a set of coincidence counting information for each set of counting information that has been retrieved, and then stores the generated sets of coincidence counting information roughly in the chronological order in the coincidence counting information storing unit 24b.

For example, the coincidence counting information generating unit 25 generates the coincidence counting information based on a coincidence counting information generating condition that is input by the operator. The coincidence counting information generating condition includes specification of a time window width. For example, the coincidence counting information generating unit 25 generates the coincidence counting information based on a time window width.

For example, the coincidence counting information generating unit 25 refers to the counting information storing unit 24a and, among the detector modules 14, searches for a set of counting information which has the time lag of the detection times (T) within the time window width. For example, assume that the coincidence counting information generating unit 25 retrieves sets "P11, E11, T11" and "P22, E22, T22" as the set that satisfies the coincidence counting information generating condition. In that case, the coincidence counting information generating unit 25 generates that set as the coincidence counting information and stores it in the coincidence counting information storing unit 24b. Meanwhile, the coincidence counting information generating unit 25 can generate the coincidence counting information with the use of an energy window width along with the time window width.

The body movement detecting unit 26 detects the temporal changes in the body movement of the subject P based on the time series list of the coincidence counting information generated by the coincidence counting information generating unit 25. The operations performed by the body movement detecting unit 26 are explained later in detail.

The image reconstructing unit 27 reconstructs PET images. More particularly, the image reconstructing unit 27 reads the time series list of coincidence counting information, which is stored in the coincidence counting information storing unit 24b, and performs reconstruction of a PET image. Then, the image reconstructing unit 27 stores the reconstructed PET image in the PET image storing unit 24c.

Meanwhile, the image reconstructing unit 27 can reconstruct PET images also by using the temporal changes in the body movement that are detected by the body movement detecting unit 26. In that case, for example, the image reconstructing unit analyzes the respiration cycle of the subject P from the temporal changes in the body movement that are detected by the body movement detecting unit 26 and, according to the respiration cycle, partitions the time series list of coincidence counting information into a plurality of phases (for example, partitions a single respiration cycle into 6 phases). Then, the image reconstructing unit 27 refers to the coincidence counting information included in each phase and reconstructs a PET image on a phase-by-phase basis. Herein, it is believed that, in each phase, the body movement of the subject is only small in amount. Thus, a single PET image is reconstructed using only such coincidence counting information that is not much affected by the body movement. That contributes to the enhancement in the image quality of PET images.

The system control unit 28 controls the PET apparatus 100 in entirety by controlling the gantry device 10 and the console device 20. For example, the system control unit 28 controls the imaging performed by the PET apparatus 100. Meanwhile, each of the coincidence counting information generating unit 25, the body movement detecting unit 26, the image reconstructing unit 27, and the system control unit 28 is configured with an integrated circuit such as an application specific integrated circuit (ASIC) or a field programmable gate array (FPGA), or with an electronic circuit such a central processing unit (CPU) or a micro processing unit (MPU).

Detection of Body Movement According to First Embodiment

Given below is the explanation regarding the detection of body movement according to the first embodiment. As described above, according to the first embodiment, based on the time series list of coincidence counting information, the body movement detecting unit 26 detects the temporal changes in the body movement of the subject P. More particularly, from each set of coincidence counting information specified in the time series list of coincidence counting information, the body movement detecting unit 26 calculates each pair annihilation coordinate on a line of response (LOR) and detects the temporal changes in the body movement of the subject P based on the calculated pair annihilation coordinates.

Figure 6:
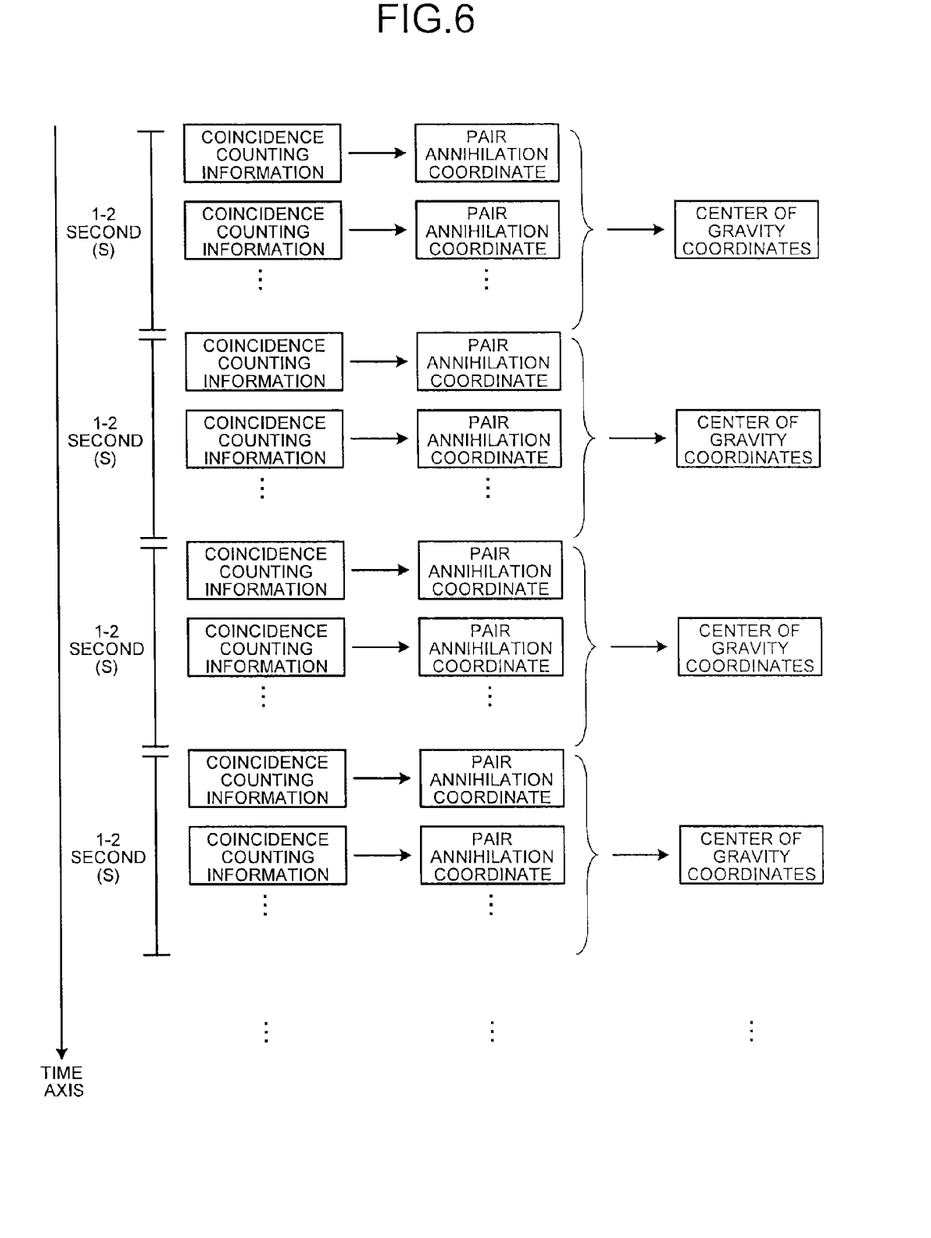
FIG. 6 is a diagram for explaining a body movement detecting unit according to the first embodiment.
Figure 7:
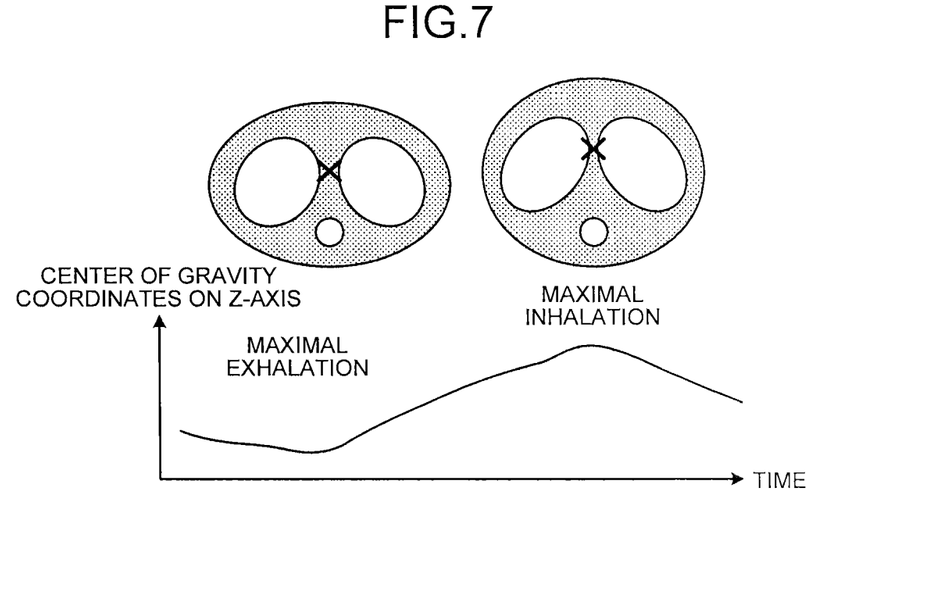
FIG. 7 is a diagram for explaining the body movement detecting unit according to the first embodiment.

FIG. 6 and FIG. 7 are diagrams for explaining the body movement detecting unit 26 according to the first embodiment. In FIG. 6, the sets of coincidence counting information that are arranged roughly in the chronological order are illustrated on a conceptual basis. For example, as illustrated in FIG. 6, the body movement detecting unit 26 partitions the time series list of coincidence counting information at predetermined time intervals (hereinafter, referred to as "frames"). In the case of obtaining respiratory phases as the temporal changes in the body movement, it is desirable that the frames are shorter than the respiration cycle of the subject P but longer than the cardiac cycle. For example, the frames are of about 1 or 2 seconds.

Then, for each predetermined frame, the body movement detecting unit 26 calculates each pair annihilation coordinate on an LOR from each set of coincidence counting information included in that frame; and accordingly calculates the average of pair annihilation coordinates (i.e., the center of gravity coordinates of the distribution of pair annihilation coordinates). Herein, the body movement detecting unit 26 calculates the pair annihilation coordinates using the TOF information. That is, the body movement detecting unit 26 calculates the detection time lag from a single set of counting information included in the coincidence counting information, and calculates pair annihilation coordinates as spatial positions of positrons on an LOR using the detection time lag. Herein, an LOR is a line that joins a set of detection positions corresponding to a pair of annihilation gamma-rays.

Then, the body movement detecting unit 26 calculates the center of gravity coordinates of the distribution of pair annihilation coordinates in each frame, and detects the temporal changes in the center of gravity coordinates. For example, of the center of gravity coordinates (x-coordinate, y-coordinate, z-coordinate) of pair annihilation coordinates, the body movement detecting unit 26 selects the coordinate axis having the largest temporal changes and plots the center of gravity coordinates on the selected coordinate axis so as to obtain the respiratory phases. For example, the body movement detecting unit 26 selects the center of gravity coordinates on the z-axis. Then, on a graph having time as the horizontal axis and having center of gravity coordinates as the vertical axis as illustrated in FIG. 7; the body movement detecting unit 26 plots, along the time axis, the center of gravity coordinates on the z-axis that are calculated for each frame. As a result, as illustrated in FIG. 7, the respiratory waveform of the subject P gets drawn on the graph. Meanwhile, in FIG. 7, schematic diagrams illustrated above the graph represent cross-sectional schematic diagrams of the chest region of the subject P. The "x" marks represent the center of gravity coordinates in the z-axis in the case of maximal exhalation and the center of gravity coordinates in the z-axis in the case of maximal inhalation. Meanwhile, for example, the graph illustrated in FIG. 7 can be displayed on the display unit 22 or be used in internal calculations.

It is described above that, of the center of gravity coordinates (x-coordinate, y-coordinate, z-coordinate) of pair annihilation coordinates, the body movement detecting unit 26 selects the coordinate axis having the largest temporal changes. However, that is not the only possible case. For example, the body movement detecting unit 26 identifies the direction having the largest temporal changes, sets a new coordinate axis oriented in the identified direction, and plots the center of gravity coordinates on the new coordinate axis so as to obtain the respiratory phases.

As described above, according to the first embodiment, the body movement information of the subject is obtained by means of direct processing for detection data. As a result, the body movement information of the subject can be obtained without difficulty. Moreover, since the body movement information is included in the detection data, it is possible to use it as may be necessary. For example, the body movement information can be used in multiple analyses.

Modification Example of First Embodiment

In the first embodiment, the explanation is given for an example in which the body movement detecting unit 26 calculates the average of pair annihilation coordinates (i.e., calculates the center of gravity coordinates) from a plurality of pair annihilation coordinates. However, that is not the only possible case. Alternatively, for example, as the statistic, the body movement detecting unit 26 can calculate the standard variation of the pair annihilation coordinates.

Figure 8:
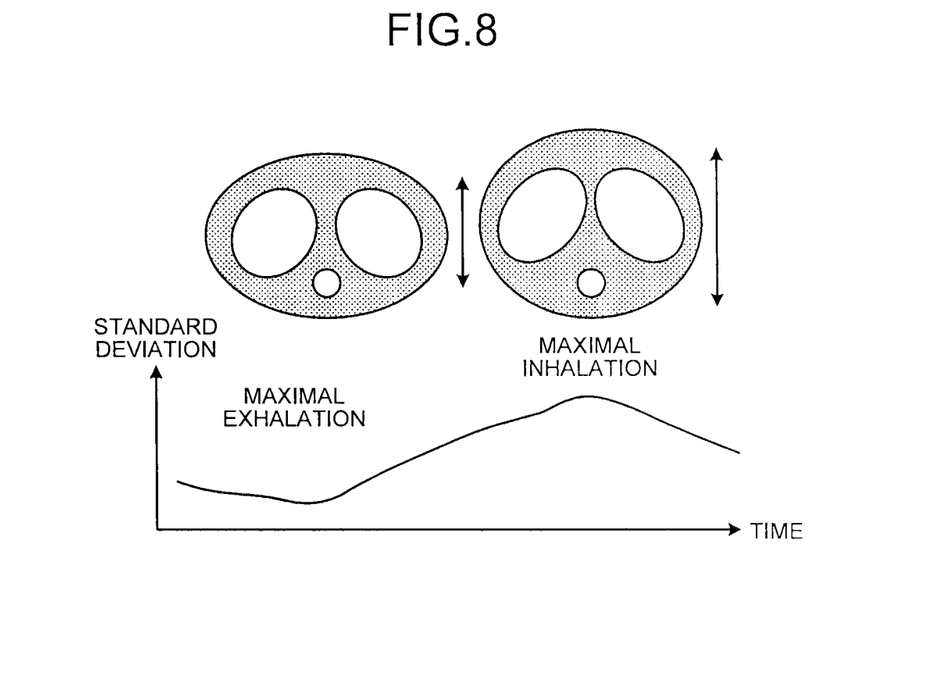
FIG. 8 is a diagram for explaining the body movement detecting unit according to a modification example of the first embodiment.

FIG. 8 is a diagram for explaining the body movement detecting unit according to a modification example of the first embodiment. The body movement detecting unit 26 calculates, for each predetermined frame, each pair annihilation coordinate on an LOR from each set of coincidence counting information included in that frame; and then calculates the standard deviation of the distribution of pair annihilation coordinates from a plurality of pair annihilation coordinates that are calculated. Herein, standard deviation points to the spread of a plurality of pair annihilation coordinates included in a frame (see an arrow illustrated in FIG. 8). The body movement detecting unit 26 calculates the standard deviation of pair annihilation coordinates for all frames; and plots the standard deviations along the time axis so as to obtain the respiratory phases. For example, on a graph having time as the horizontal axis and having standard deviation as the vertical axis as illustrated in FIG. 8, the body movement detecting unit 26 plots the standard deviations on the z-axis that are calculated for all frames. As a result, as illustrated in FIG. 8, the respiratory waveform of the subject P gets drawn on the graph.

Second Embodiment

Given below is the explanation of a second embodiment. In the first embodiment, the explanation is given for a method in which the temporal changes in the body movement are detected with the use of all sets of coincidence counting information included in the time series list of coincidence counting information. However, that is not the only possible case. In the second embodiment, the explanation is given for a method in which the temporal changes in the body movement are detected with the use of only some of the sets of coincidence counting information.

Figure 9:
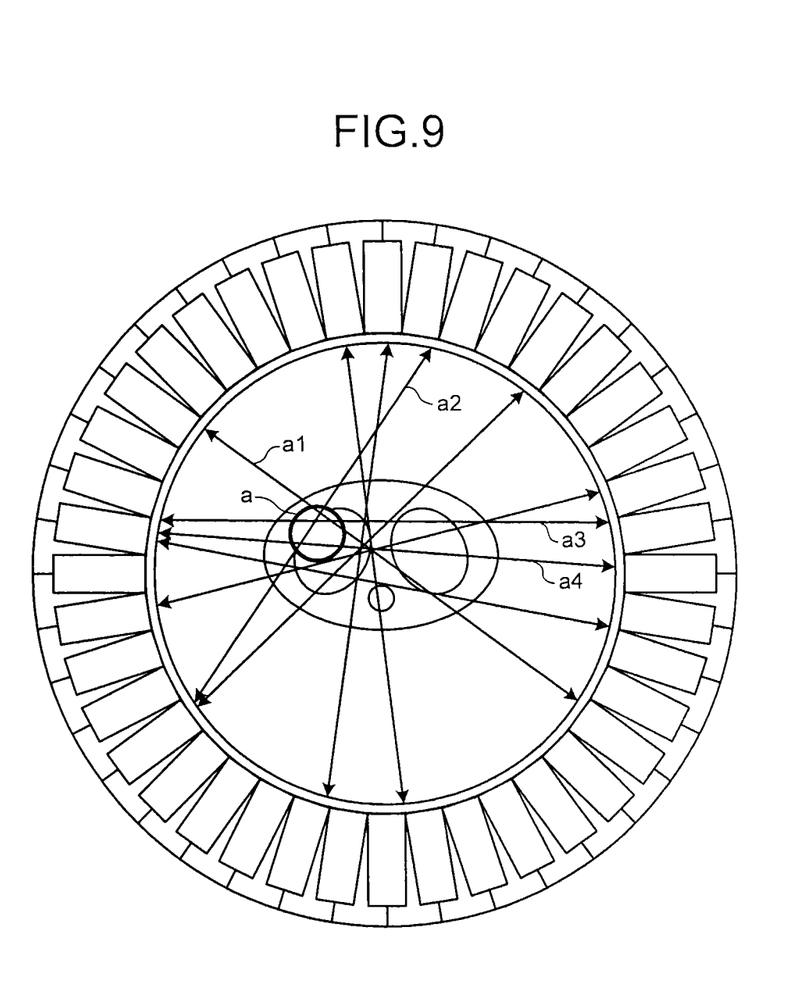
FIG. 9 is a diagram for explaining the body movement detecting unit according to a second embodiment.

FIG. 9 is a diagram for explaining the body movement detecting unit 26 according to the second embodiment. FIG. 9 is a schematic diagram of a cross-sectional surface of the chest region of the subject P that is surrounded by detectors. A black circle "a" represents the heart of the subject P. In the second embodiment, the cardiac phases are obtained as the temporal changes in the body movement.

For example, from the time series list of coincidence counting information, the body movement detecting unit 26 selects only such a plurality of sets of coincidence counting information for each of which the LOR passes through the heart of the subject P. Herein, by referring to the posture of the subject P who is lying down on the couch top 11 or by referring to the body type of the subject P, it is possible to roughly identify in advance the LORs (i.e., the sets of detection positions) that pass through the heart. Hence, from the time series list of coincidence counting information, the body movement detecting unit 26 selects only the coincidence counting information that corresponds to the detection positions of the sets of detection positions identified in advance. For example, in FIG. 9, LORs a1 to a4 pass through the heart.

Then, from each selected set of coincidence counting information, the body movement detecting unit 26 calculates each pair annihilation coordinate on each LOR and, in an identical manner to the first embodiment, detects the temporal changes in the body movement of the subject P based on the plurality of pair annihilation coordinates that are calculated.

Modification Example of Second Embodiment

As a modification example of the second embodiment, for example, the explanation is given about a technique in which the respiratory phases are obtained as the temporal changes in the body movement, while the effect of the cardiac phases is eliminated. In the first embodiment, the explanation is given regarding the case in which the respiratory phase can be obtained as the temporal changes in the body movement. However, in case the radiopharmaceutical agent gets accumulated in the heart, there is a possibility that the effect of the cardiac phases gets reflected in the temporal changes in the body movement. In that case, on the respiratory waveform representing the respiratory phases, a waveform that represents the cardiac phases having a shorter cycle than the respiration cycle appears as noise.

In that regard, for example, from the time series list of coincidence counting information, the body movement detecting unit 26 selects only such a plurality of sets of coincidence counting information for each of which the LOR does not pass through the heart of the subject P. That is, from the time series list of coincidence counting information, the body movement detecting unit 26 excludes the coincidence counting information corresponding to the sets of detection positions identified in advance as the LORs passing through the heart, and selects the remaining coincidence counting information. For example, in FIG. 9, LORs other than the LORs a1 to a4 do not pass through the heart.

Then, from each selected set of coincidence counting information, the body movement detecting unit 26 calculates each pair annihilation coordinate on each LOR and, in an identical manner to the first embodiment, detects the temporal changes in the body movement of the subject P based on a plurality of pair annihilation coordinates that are calculated.

As described above, according to the second embodiment, the temporal changes in the body movement are detected by selecting only some of the coincidence counting information. As a result, it becomes possible to detect the temporal changes in the body movement by focusing attention on a particular body part or to detect the temporal changes in the body movement by eliminating the effect of a particular body part.

Other Embodiments

In the embodiments described above, the PET apparatus 100 is assumed to have the configuration illustrated in FIG. 1. However, that is not the only possible configuration. Alternatively, for example, the counting information collecting unit 15 can be disposed in the console device 20. Conversely, the coincidence counting information generating unit 25 can be disposed in the gantry device 10. Moreover, the variety of data stored in the data storing unit 24 can either be held in the gantry device 10 or be held in the console device 20. Meanwhile, each type of data can be held in the PET apparatus 100 for an arbitrary period of time.

Furthermore, for example, the body movement detecting unit 26 can be disposed in an image processing apparatus other than the PET apparatus 100. In that case, for example, the image processing apparatus includes a coincidence counting information storing unit that is used to store a time series list of coincidence counting information; a body movement detecting unit that detects the temporal changes in the body movement of the subject based on the time series list of coincidence counting information; and an image reconstructing unit that refers to the temporal changes in the body movement of the subject and accordingly reconstructs images of the subject from the time series list of coincidence counting information. Meanwhile, the temporal changes in the body movement of the subject can be used for purposes other than image reconstruction. In that case, the image reconstructing unit becomes redundant.

According to the positron emission computed tomography apparatus and the image processing apparatus thereof of at least one of the above-described embodiments, body movement information of a subject can be obtained without difficulty.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A positron emission computed tomography apparatus comprising:
a detector configured to detect annihilation radiations released from a subject;
a coincidence counting information generating unit configured to, from a counting information list that is generated from output signals of the detector, search for sets of counting information which counted a pair of annihilation radiations at substantially the same time, generate a set of coincidence counting information for each retrieved set of counting information, and generate a time series list of coincidence counting information;
a body movement detecting unit configured to, from each set of coincidence counting information included in the time series list of coincidence counting information, calculate each pair annihilation coordinate on a line of response (LOR) and detect temporal changes in the body movement of the subject based on a plurality of pair annihilation coordinates that is calculated; and
an image reconstructing unit configured to partition the time series list of coincidence counting information into a plurality of phases based on the temporal changes in the body movement of the subject detected by the body movement detecting unit, and reconstruct an image of each phase by referring to the coincidence counting information included in each phase, wherein
the body movement detecting unit partitions the time series list of coincidence counting information at predetermined time intervals, calculates, at each of the predetermined time intervals, center of gravity coordinates of pair annihilation coordinates that are calculated from coincidence counting information included in the time interval, identifies a direction having the largest temporal changes of the center of gravity coordinates, and detects temporal changes in the body movement of the subject based on temporal changes of the center of gravity coordinates in the identified direction.

2. The positron emission computed tomography apparatus according to claim 1, wherein the body movement detecting unit either calculates an average in each time interval or a standard deviation in each time interval.

3. A positron emission computed tomography apparatus comprising:
   a detector configured to detect annihilation radiations released from a subject;
   a coincidence counting information generating unit configured to, from a counting information list that is generated from output signals of the detector, search for sets of counting information which counted a pair of annihilation radiations at substantially the same time, generate a set of coincidence counting information for each retrieved set of counting information, and generate a time series list of coincidence counting information;
   a body movement detecting unit configured to, from the time series list of coincidence counting information, select a plurality of sets of coincidence information for each of which an LOR passes through a predetermined body part inside the subject, calculate each pair annihilation coordinate on an LOR from each selected set of coincidence counting information, and detect temporal changes in the body movement of the subject based on a plurality of calculated pair annihilation coordinates; and
   an image reconstructing unit configured to partition the time series list of coincidence counting information into a plurality of phases based on the temporal changes in the body movement of the subject detected by the body movement detecting unit, and reconstruct an image of each phase by referring to the coincidence counting information included in each phase, wherein,
   the body movement detecting unit partitions the time series list of coincidence counting information at predetermined time intervals, calculates, at each of the predetermined time intervals, center of gravity coordinates of pair annihilation coordinates that are calculated from coincidence counting information included in the time interval, identifies a direction having the largest temporal changes of the center of gravity coordinates, and detects temporal changes in the body movement of the subject based on temporal changes of the center of gravity coordinates in the identified direction.

4. The positron emission computed tomography apparatus according to claim 3, wherein the body movement detecting unit either calculates an average in each time interval or a standard deviation in each time interval.

5. A positron emission computed tomography apparatus comprising:
   a detector configured to detect annihilation radiations released from a subject;
   a coincidence counting information generating unit configured to, from a counting information list that is generated from output signals of the detector, search for sets of counting information which counted a pair of annihilation radiations at substantially the same time, generate a set of coincidence counting information for each retrieved set of counting information, and generate a time series list of coincidence counting information;
   a body movement detecting unit configured to, from the time series list of coincidence counting information, select a plurality of sets of coincidence information for each of which an LOR does not pass through a predetermined body part inside the subject, calculate each pair annihilation coordinate on an LOR from each selected set of coincidence counting information, and detect temporal changes in the body movement of the subject based on a plurality of calculated pair annihilation coordinates; and
   an image reconstructing unit configured to partition the time series list of coincidence counting information into a plurality of phases based on the temporal changes in the body movement of the subject detected by the body movement detecting unit, and reconstruct an image of each phase by referring to the coincidence counting information included in each phase, wherein,
   the body movement detecting unit partitions the time series list of coincidence counting information at predetermined time intervals, calculates, at each of the predetermined time intervals, center of gravity coordinates of pair annihilation coordinates that are calculated from coincidence counting information included in the time interval, identifies a direction having the largest temporal changes of the center of gravity coordinates, and detects temporal changes in the body movement of the subject based on temporal changes of the center of gravity coordinates in the identified direction.

6. The positron emission computed tomography apparatus according to claim 5, wherein the body movement detecting unit either calculates an average in each time interval or a standard deviation in each time interval.

7. An image processing apparatus comprising:
   a coincidence counting information storing unit configured to store a time series list of coincidence counting information which represents sets of counting information that substantially concurrently counted a pair of annihilation radiations released from a subject;
   a body movement detecting unit configured to from each set of coincidence counting information included in the time series list of coincidence counting information, calculate each pair annihilation coordinate on a line of response (LOR) and detect temporal changes in the body movement of the subject based on a plurality of pair annihilation coordinates that is calculated; and
   an image reconstructing unit configured to partition the time series list of coincidence counting information into a plurality of phases based on the temporal changes in the body movement of the subject detected by the body movement detecting unit, and reconstruct an image of the each phase by referring to the coincidence counting information included in each phase, wherein
   the body movement detecting unit partitions the time series list of coincidence counting information at predetermined time intervals, calculates, at each of the predetermined time intervals, center of gravity coordinates of pair annihilation coordinates that are calculated from coincidence counting information included in the time interval, identifies a direction having the largest temporal changes of the center of gravity coordinates, and detects temporal changes in the body movement of the subject based on temporal changes of the center of gravity coordinates in the identified direction.

8. An image processing apparatus comprising:
   a coincidence counting information storing unit configured to store a time series list of coincidence counting information which represents sets of counting information that substantially concurrently counted a pair of annihilation radiations released from a subject;
   a body movement detecting unit configured to, from the time series list of coincidence counting information, select a plurality of sets of coincidence information for each of which an LOR passes through a predetermined body part inside the subject, calculate each pair annihilation coordinate on an LOR from each selected set of coincidence counting information, and detect temporal changes in the body movement of the subject based on a plurality of calculated pair annihilation coordinates; and an image reconstructing unit configured to partition the time series list of coincidence counting information into a plurality of phases based on the temporal changes in the body movement of the subject detected by the body movement detecting unit, and reconstruct an image of the each phase by referring to the coincidence counting information included in each phase, wherein the body movement detecting unit partitions the time series list of coincidence counting information at predetermined time intervals, calculates, at each of the predetermined time intervals, center of gravity coordinates of pair annihilation coordinates that are calculated from coincidence counting information included in the time interval, identifies a direction having the largest temporal changes of the center of gravity coordinates, and detects temporal changes in the body movement of the subject based on temporal changes of the center of gravity coordinates in the identified direction.

9. An image processing apparatus comprising:

a coincidence counting information storing unit configured to store a time series list of coincidence counting information which represents sets of counting information that substantially concurrently counted a pair of annihilation radiations released from a subject;

a body movement detecting unit configured to, from the time series list of coincidence counting information, select a plurality of sets of coincidence information for each of which an LOR does not pass through a predetermined body part inside the subject, calculate each pair annihilation coordinate on an LOR from each selected set of coincidence counting information, and detect temporal changes in the body movement of the subject based on a plurality of calculated pair annihilation coordinates; and an image reconstructing unit configured to partition the time series list of coincidence counting information into a plurality of phases based on the temporal changes in the body movement of the subject detected by the body movement detecting unit, and reconstruct an image of the each phase by referring to the coincidence counting information included in each phase, wherein the body movement detecting unit partitions the time series list of coincidence counting information at predetermined time intervals, calculates, at each of the predetermined time intervals, center of gravity coordinates of pair annihilation coordinates that are calculated from coincidence counting information included in the time interval, identifies a direction having the largest temporal changes of the center of gravity coordinates, and detects temporal changes in the body movement of the subject based on temporal changes of the center of gravity coordinates in the identified direction.

\* \* \* \* \*